United States Patent
Willard et al.

[11] Patent Number: 5,980,530
[45] Date of Patent: Nov. 9, 1999

[54] STENT DELIVERY SYSTEM

[76] Inventors: Martin R. Willard, 18533 87th Ave. North, Maple Grove, Minn. 55311; John H. Randby, 4144 Cashell Glen, Eagan, Minn. 55122

[21] Appl. No.: 08/702,149

[22] Filed: Aug. 23, 1996

[51] Int. Cl.⁶ .................................................. A61F 11/00
[52] U.S. Cl. .......................... 606/108; 606/195; 606/198
[58] Field of Search ................................. 606/108, 195, 606/198, 191, 194; 604/96

[56] References Cited

U.S. PATENT DOCUMENTS

| | | |
|---|---|---|
| 4,328,056 | 5/1982 | Snooks . |
| 4,338,942 | 7/1982 | Fogarty . |
| 4,423,725 | 1/1984 | Baran et al. . |
| 4,608,984 | 9/1986 | Fogarty . |
| 4,733,665 | 3/1988 | Palmaz . |
| 4,735,665 | 4/1988 | Miyauchi . |
| 4,740,207 | 4/1988 | Kreamer . |
| 4,744,366 | 5/1988 | Jang . |
| 4,848,343 | 7/1989 | Wallstein et al. . |
| 4,875,480 | 10/1989 | Imbert . |
| 4,950,227 | 8/1990 | Savin et al. ............................ 606/192 |
| 5,007,926 | 4/1991 | Derbyshire . |
| 5,026,377 | 6/1991 | Burton et al. . |
| 5,037,392 | 8/1991 | Hillstead . |
| 5,049,132 | 9/1991 | Shaffer et al. . |
| 5,108,416 | 4/1992 | Ryan et al. ............................. 606/194 |
| 5,116,318 | 5/1992 | Hillstead . |
| 5,158,548 | 10/1992 | Lau et al. . |
| 5,226,880 | 7/1993 | Martin . |
| 5,226,889 | 7/1993 | Sheiban . |
| 5,242,399 | 9/1993 | Lau et al. . |
| 5,290,306 | 3/1994 | Trotta et al. . |
| 5,342,305 | 8/1994 | Shonk . |
| 5,344,402 | 9/1994 | Crocker . |
| 5,344,426 | 9/1994 | Lau et al. . |
| 5,358,487 | 10/1994 | Miller . |
| 5,378,237 | 1/1995 | Boussignac et al. . |
| 5,403,341 | 4/1995 | Solar . |
| 5,405,380 | 4/1995 | Gianotti et al. . |
| 5,409,495 | 4/1995 | Osborn . |
| 5,415,664 | 5/1995 | Pinchuk . |
| 5,445,646 | 8/1995 | Euteneuer et al. ...................... 606/198 |
| 5,447,497 | 9/1995 | Sogard et al. . |
| 5,453,090 | 9/1995 | Martinez et al. . |
| 5,458,615 | 10/1995 | Klemm et al. . |
| 5,470,313 | 11/1995 | Crocker et al. . |
| 5,507,768 | 4/1996 | Lau et al. . |
| 5,512,051 | 4/1996 | Wang et al. . |
| 5,534,007 | 7/1996 | St. Germain et al. . |
| 5,536,252 | 7/1996 | Imran et al. . |
| 5,591,222 | 1/1997 | Susawa et al. .............................. 623/1 |
| 5,643,278 | 7/1997 | Wijay ..................................... 606/198 |

FOREIGN PATENT DOCUMENTS

| | | |
|---|---|---|
| 0 442 657 A2 | 8/1991 | European Pat. Off. . |
| 0 553 960 A1 | 8/1993 | European Pat. Off. . |
| 0 707 837 A1 | 4/1996 | European Pat. Off. . |
| WO 90/05554 | 5/1990 | WIPO . |
| WO96/03072 A1 | 2/1996 | WIPO . |
| WO96/03092 A1 | 2/1996 | WIPO . |

OTHER PUBLICATIONS

Julio C. Palmaz et al., 156 *Radiology* 73 (1985), Expandable Intraluminal Graft: A Preliminary Study.

*Primary Examiner*—Richard J. Apley
*Assistant Examiner*—Justine R. Yu

[57] ABSTRACT

A stent delivery system to facilitate introduction and placement of a stent, including a catheter having an expandable distal portion constructed and arranged for expanding the outer diameter of the catheter from a contracted state to an expanded state: a stent positioned around the distal portion of the catheter having a contracted condition and being expandable to an expanded condition, and being sized in the contracted condition to closely surround the catheter in the contracted state, the expandable distal portion of the catheter including a balloon within which there is included on the catheter shaft at least one body of a diameter larger than the catheter shaft to which the stent and balloon are fitted, as by crimping, for holding the stent in place until it is released therefrom by expansion of the balloon.

38 Claims, 4 Drawing Sheets

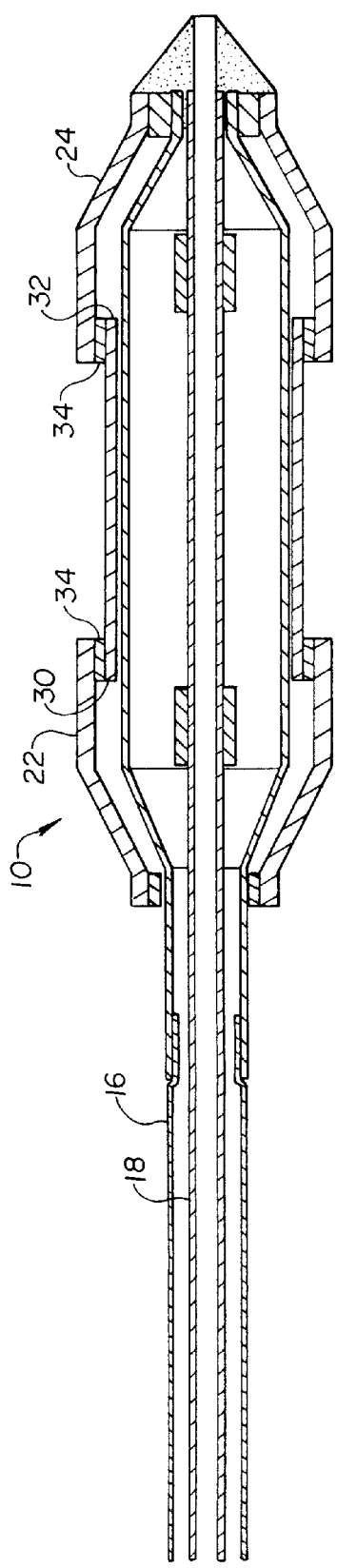
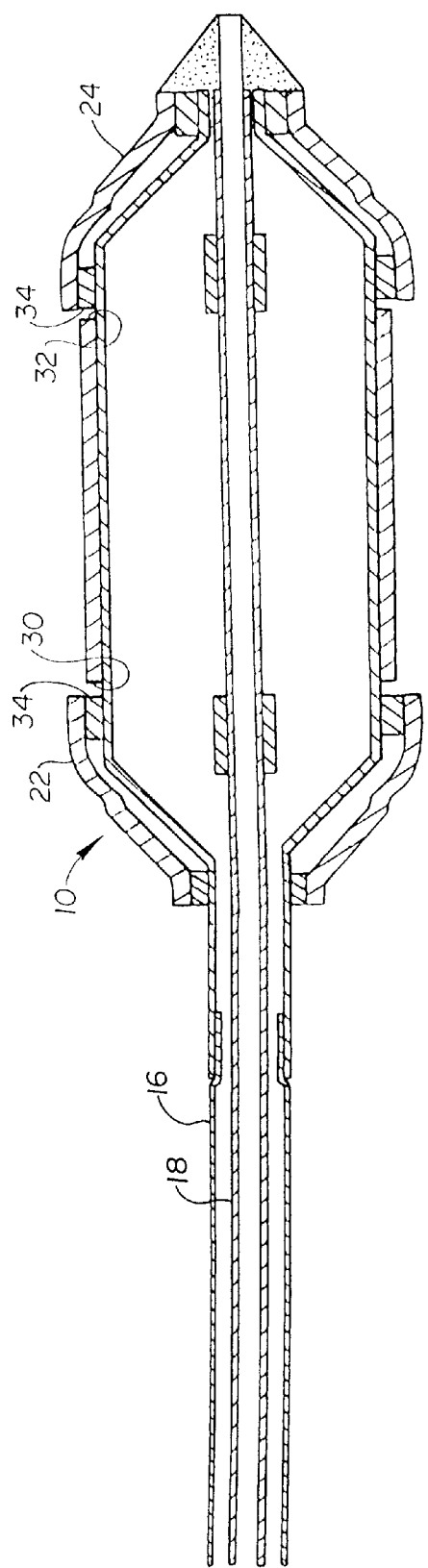
Fig. 1
Fig. 2

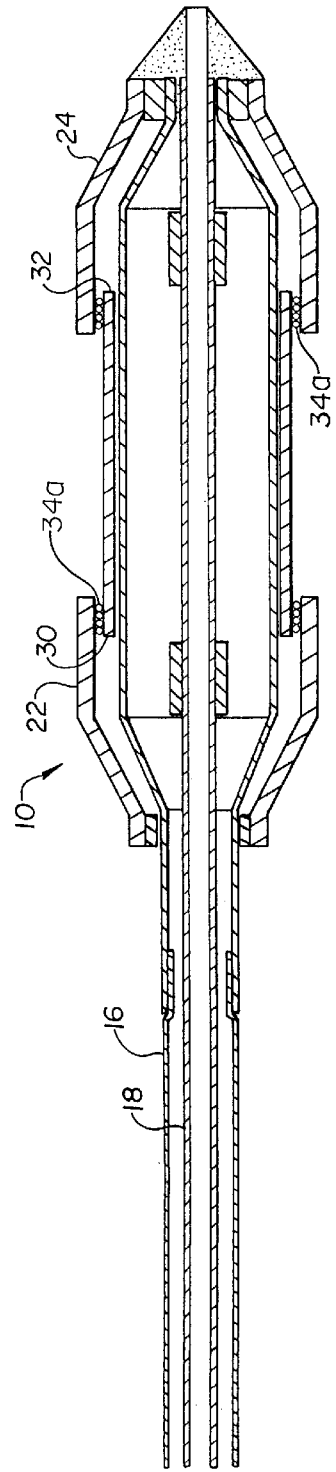
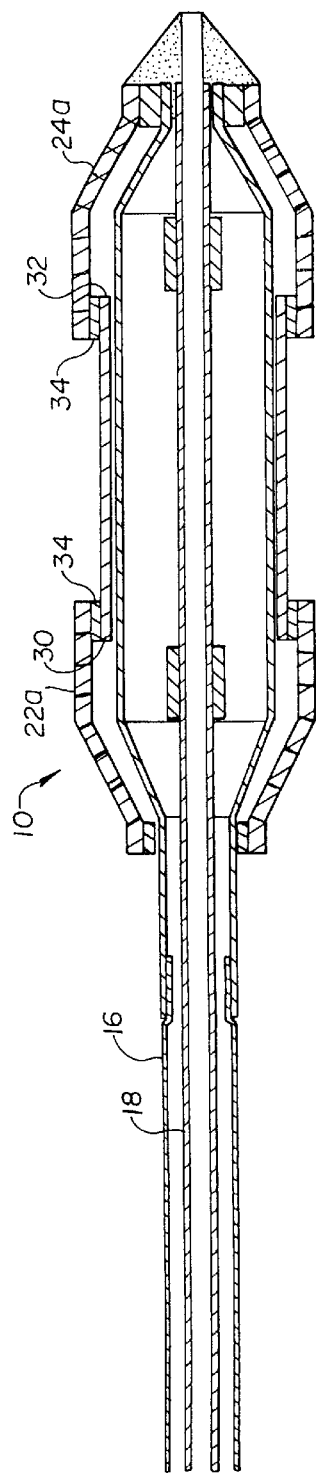
Fig. 3
Fig. 4

STENT DELIVERY SYSTEM

BACKGROUND OF THE INVENTION

In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid or gas at relatively high pressures, such as greater than about four atmospheres, to radially compress the arthrosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be injury to or restenosis of the artery, which either necessitates another angioplasty procedure, a surgical by-pass operation, or some method of repairing or strengthening the area. To strengthen the area and help prevent restenosis, a physician can implant an intravascular prosthesis for maintaining vascular patency, commonly called a stent, inside the artery at the lesion. The stent is expanded to a larger diameter for placement in the vasculature, often by the balloon portion of the catheter. Stents delivered to a restricted coronary artery, expanded to a larger diameter by a balloon catheter, and left in place in the artery at the site of a dilated lesion are shown in U.S. Pat. No. 4,740,207 to Kreamer and U.S. Pat. No. 5,007,926 to Derbyshire, the content of which is incorporated herein by reference. Palmaz et al., 156 *Radiology* 73 (1985) and U.S. Pat. No. 4,733,665 describe introduction of a stent over a balloon catheter (incorporated herein by reference). A preferred stent for use with this invention is shown in PCT Application Ser. No. 960 3092 A1, published Feb. 8, 1996, the content of which is incorporated herein by reference.

The present invention is particularly directed to improved arrangements for releasably attaching the stent to the catheter to facilitate delivery thereof.

SUMMARY OF THE INVENTION

This invention concerns apparatus suitable for delivery of stents to body cavities. In general, stents are prosthetic devices which can be positioned within a body cavity, for example, a blood vessel of the body of a living human or in some other difficultly accessible place. The stent prosthesis is formed of a generally tubular body, the diameter of which can be decreased or increased. Stents are particularly useful for permanently widening a vessel which is either in a narrowed state, or internally supporting a damaged vessel. Such stents are typically introduced into the body cavity by use of a catheter. The catheter is usually of the balloon catheter type in which the balloon is utilized to expand the stent, which is positioned over the balloon, to place it in a selected location in the body cavity. The present invention is particularly directed to improved arrangements for releasably attaching the stent to the catheter to facilitate delivery thereof. The stent is held in place on the catheter by means of at least one removable end covering means over the stent, the stent having been fitted to the catheter over the balloon, as by crimping. Most specifically, this invention is directed to improved modifications to the subject matter of the Savin U.S. Pat. No. 4,950,227 which is incorporated herein by reference.

In particular, the invention is directed to an improved stent delivery system designed to securely hold a stent over the balloon on a catheter and to protect the stent from deformation, damage or premature release during delivery intraluminally. The stent is formed to its lowest geometrical diameter when loaded. Rings or coils are placed over the ends of the stent to retain them and hold them to the balloon (unexpanded) with little or no relative movement between the ID of the stent and the OD of the balloon/catheter arrangement. The restrictive rings or coils are each attached to an elastomeric sleeve. The other end of the sleeves are respectively attached to the catheter. When the balloon under the stent is inflated, the stent pushes out of the rings/coils and the sleeves are pushed down the balloon cones to allow the stent to deploy. Since most stents which are deformed to a low diameter will increase in diameter somewhat after being deformed (spring back), the rings/coils prevent spring back and increase the friction fit between the stent and balloon.

In a different embodiment, a polymer tube may be formed into a spiral, as by cutting molding or extruding, except for about 1–2 mm on one end; its entire length need only be about 1–2 cm. The uncut portion of the spiral, i.e., the ring end is placed over the end of the stent to retain it as already described. The other end of the coil, a portion of which may be uncut also to form a ring is attached to the catheter.

Modifications to this embodiment include replacement of the plastic ring with a metal ring or coil and replacement of the sleeve/ring with a metal or plastic coil or coiled ribbon. Short balloon cone length and/or tension on the spiral can help the spiral move off the stent when the balloon is inflated.

BRIEF DESCRIPTION OF THE FIGURES

FIG. 1 is a view, in longitudinal section, of the distal end portion of a balloon catheter having a stent fixed to the catheter by being crimped thereto over the balloon, the ends of the stent being held by a first embodiment of the invention;

FIG. 2 is similar to FIG. 1 in which the stent has been released;

FIG. 3 is a view of a modification of the embodiment shown in FIGS. 1 and 2;

FIG. 4 is a view of another modification to the embodiment of FIGS. 1 and 2;

DESCRIPTION OF THE PREFERRED EMBODIMENTS

Figure 5:
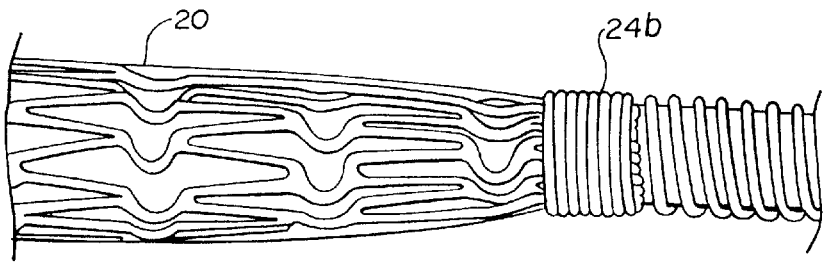
FIG. 5 is a showing of another embodiment of the invention used to hold the ends of the stent.

Referring to FIGS. 1 and 2, a stent delivery system 10 includes a catheter such as an over-the-wire or rapid exchange. Balloon catheters are preferred herein as best examples of catheters having an expandable distal end portion constructed and arranged for expanding the outer diameter of the catheter from a contracted state to an expanded state. A balloon 14 is fixed to the distal end of the catheter by adhesive attachment of the proximal end to the outer shaft 16 of the catheter and the distal end to the inner shaft 18 of the catheter. Other arrangements known in the art may be used. Balloon 14 is shown in FIG. 1 in its contracted state and in FIG. 2 in its expanded state. A stent 20 is fixed about balloon 14 by two overlying retaining sleeves 22 and 24.

Various types of stents may be used with balloon expansion. For example, the stent may be a self-expanding stent which upon release self-expands and is further expanded or is merely aided in release by balloon expansion from the sleeves. Such stents may self-expand elastically or may be thermally induced such as stents formed of nitinol or other shape memory metals or materials.

Any kind of stent may be delivered by the system of the invention, including plastically deformable or elastically deformable and they may be of any configuration or structure so long as they can be loaded at a low diameter and deployed at a larger diameter, i.e., have a contracted condition and being expandable to an expanded condition of large diameter.

Stent 20 may be any of the various types known in the art, either balloon expandable or self-expandable. Exemplary stents are shown in U.S. Pat. No. 4,735,665; U.S. Pat. No. 4,950,227; EPO application 707 837 A1, and U.S. Pat. No. 5,445,646. All of these patents are incorporated herein by reference and are intended to be exemplary only and not limiting. Various materials including stainless steel, tantalum, shape memory alloys and plastic may be used.

Stent 20 is radially compressed, as by crimping to a contracted condition, against balloon 14 to a relatively small loaded diameter having an OD of 0.044 inches for example, although it has a larger released diameter in the expanded condition.

Sleeves 22 and 24 may be formed of polyurethane tubing or the like, having for example an ID of 0.032–0.038 inches and a wall thickness of 0.002–0.004 inches, for example, and are axially fixed along catheter 10 to the proximal end of balloon 14 at 22 and to the distal end of balloon 14 at 24 by means of polyurethane adhesive 26. The distal end also includes a tapered end 28 which may be formed of the same adhesive.

The sleeves may be of an expandable material, preferable elastomers such as polyurethane, silicone, latex or polyether amide, by way of example only. The material should be formable into a thin walled tube. Only one sleeve may be provided at one end of the stent, preferably the distal end. However, the use of a pair of sleeves, one at each end of the stent, is most preferred.

Sleeves 22 and 24 overlap stent 20 at each of its ends 30 and 32, respectively. For example, the overlap may be 1–1.5 mm. Reinforcing rings 34 are included under the overlapping portions of sleeves 22 and 24 and in contact with the stent ends. The rings may be attached to the sleeves with adhesive such as a polyurethane adhesive. The rings may be plastic, such as polyimide or polyethylene, or metal, such as platinum, gold, stainless steel or nitinol, and may be 0.001–0.004 inches and the ID of the ring is to match the desired OD of the stent. The function of the rings is to compress the stent and hold it down.

Referring to FIG. 2, in its expanded state balloon 14 has an enlarged diameter with tapered portions 36 and 38 at each end thereof. Stent 20 is released from sleeves 22 and 24 upon expansion of balloon 14 by pulling out of the sleeves and the bunching back of the sleeves. As seen in FIG. 2 the stent deploys. The sleeves contract about balloon 14 when it is deflated. Deflation allows balloon 14 and sleeves 22 and 24 along with catheter 10 to be axially removed from the body.

In situations where the stent OD is large relative to the stretched ID of the sleeves; such as 0.060 inches as compared to 0.032–0.038, the fit between the sleeve ID and the balloon end portion tends to be so large as to create difficulty in forming an acceptable profile for the catheter and it is difficult to sufficiently increase the OD of the balloon catheter to provide adequate interference fit of the stent to the balloon. The rings provide increased friction fit in such instances and aid in controlling spring-back of the crimped stent.

In assembling the polyurethane sleeves, they can be temporarily swelled by exposure to a solvent such as toluene, alcohol, or others as known in the art, then pushed on the ends of the stent. The sleeves are then bonded to the balloon ends with a polyurethane adhesive or the like.

Other embodiments are within the claims to this invention. For example, referring to FIG. 3, the rings 34 seen in FIGS. 1 and 2 may take the form of wire coils 34a which may for example be stainless steel or nitinol or polyamides such as nylon.

Referring to FIG. 4, the sleeves 22 and 24 of the preceding Figures may take the form of spiral coils of plastic 22a and 24a such as polyamide or polyethylene or polyimide for example. The spiral may be cut only partially into the body as a spiral cut or it may be cut all the way through as shown.

Figure 6:
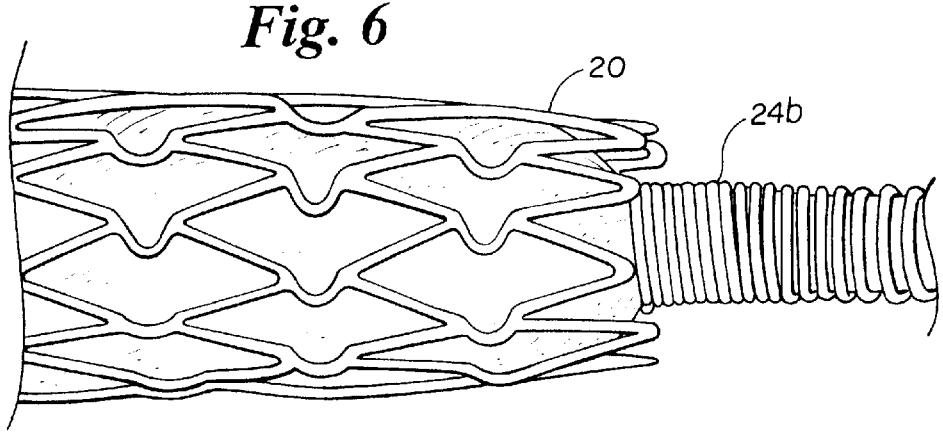
FIG. 6 is a showing of the FIG. 5 arrangement in which the stent has been released.

Referring to FIGS. 5 and 6, the sleeves 22 and 24 of the preceding Figures may be replaced by metal such as stainless steel or nitinol coils 22b (not shown) and 24b, for example. FIG. 5 shows such coils engaging stent 20 in the loaded or crimped position, ready for delivery. FIG. 6 shows the coils retracted by balloon expansion with stent 20 partially expanded and ready to be deployed.

Figure 7:
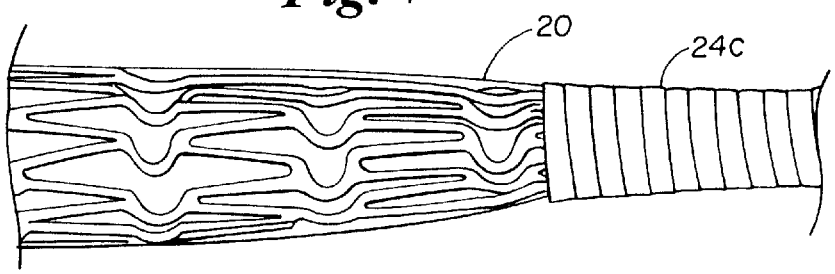
FIG. 7 is a showing of yet another embodiment of the invention used to hold the ends of the stent.
Figure 8:
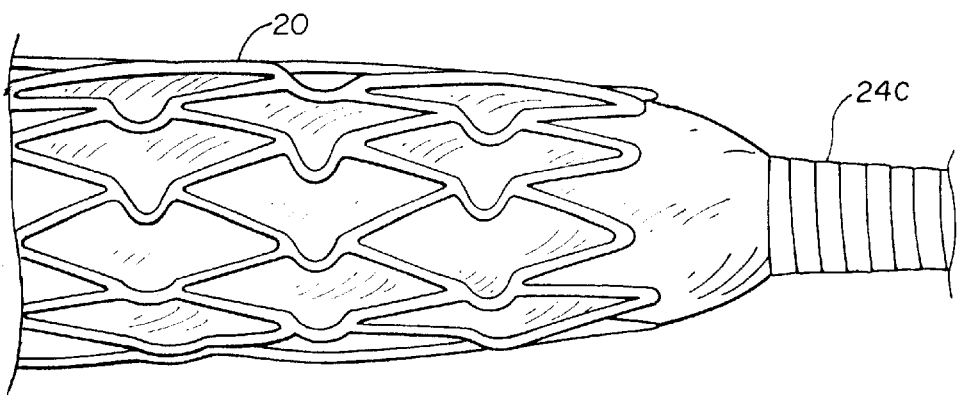
FIG. 8 is a showing of the FIG. 7 arrangement in which the stent has been released.

Referring to FIGS. 7 and 8, metal coils 22b (not shown) and 24b of FIGS. 5 and 6 may take the form of flat coiled ribbons 22c and 24c in either metal or plastic of the types already described. In FIG. 7 the coiled ribbons 22c and 24c are shown engaging the stent 20 in the loaded or crimped position, ready for delivery. FIG. 8 shows them retracted by balloon expansion with stent 20 partially expanded ready for deployment.

Figure 9:
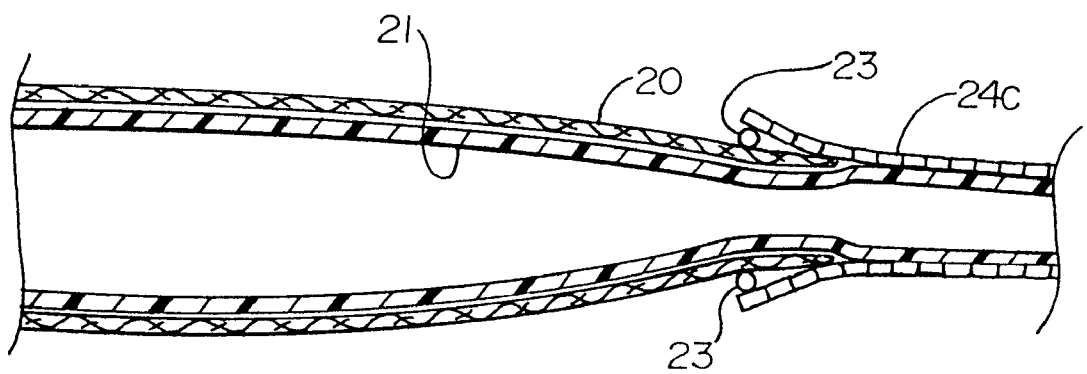
FIG. 9 is a partial cross-sectional view of FIG. 7.

FIG. 9 is a cross-sectional view of FIG. 7. It illustrates the coil 24c and a ring 23 attached to the inside of the end of the coil 24c, the combination of which secures the end of the stent 20 onto the balloon 21 prior to expansion of the balloon.

Any body compatible metal and plastic having the requisite strength characteristics, and/or other physical characteristics may be used in the various embodiments of this invention.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent delivery system comprising:
   a catheter comprising an expandable distal portion, having an outer diameter, constructed and arranged for expanding the outer diameter of said expandable distal portion from a contracted state to an expanded state;
   a stent positioned around said distal portion of said catheter, said stent having a contracted condition and being expandable to an expanded condition, and being sized in said contracted condition to closely surround said catheter in the contracted state, said stent having a first end and a second end, wherein at least a portion of the stent is lying over said expandable portion of said catheter;
   a sleeve in the region of said distal portion of said catheter and positioned around said catheter, the sleeve having a first end anchored to said catheter, and a second end lying over said first end of said stent;
   a ring attached to said second end of said sleeve and positioned around said stent first end;
   said sleeve and ring securing said first end of said stent on said catheter when said catheter is in the contracted state, said catheter and stent cooperatively constructed and arranged for expansion of said catheter from said contracted state to said expanded state and to cause said sleeve and ring to simultaneously slide relatively axially from over said stent, thereby releasing said first end of the stent from said catheter.

2. The stent delivery system of claim 1 wherein said expansible distal portion comprises a balloon mounted on a shaft of the catheter.

3. The stent delivery system of claim 2 wherein said stent is expanded by expansion of said balloon.

4. The stent delivery system of claim 1, said sleeve being formed from polyurethane.

5. The stent delivery system of claim 1, said sleeve being formed from any elastomer able to be expanded with a balloon angioplasty catheter, and formable into a thin-walled tube.

6. The stent delivery system of claim 1, said end of said first end of the stent being a distal end, wherein said sleeve fixes said stent at the distal end of said stent.

7. The stent delivery system of claim 1, said sleeve being formed in the shape of a cylinder.

8. The stent delivery system of claim 1, said ring being formed in the shape of a coil.

9. The stent delivery system of claim 8 wherein said ring is plastic.

10. The stent delivery system of claim 8 wherein the coil is metal.

11. The stent delivery system of claim 1 wherein the ring is metal.

12. The stent delivery system of claim 1 wherein the ring is plastic.

13. A stent delivery system comprising:
    a catheter comprising an expandable distal portion constructed and arranged for expanding the outer diameter of said catheter from a contracted state to an expanded state;
    a stent positioned around said distal portion of said catheter, said stent having a contracted condition and being expandable to an expanded condition, and being sized in said contracted condition to closely surround said catheter in the contracted state, said stent having a first and second end portion lying over said expandable portion of said catheter;
    first and second sleeves in the region of said distal portion of said catheter positioned around said catheter, each having a first end anchored to said catheter and a second end lying over said first and second ends of said stent;
    first and second rings, each being respectively attached to said second ends of said first and second sleeves and positioned around said ends of said stent;
    said first sleeve and first ring and said second sleeve and second ring separately engaging said stent at said first end and said second end respectively;
    said first and second sleeves and rings securing said ends of said stent on said catheter when said catheter is in the contracted state, said catheter and stent cooperatively constructed or arranged for expansion of said catheter from said contracted state to said expanded state to cause expansion of said stent, including said first and second ends of said stent, from said contracted condition to said expanded condition, and thereby causing said first sleeve and first ring to simultaneously slide relatively axially from over the first end of the stent and said second sleeve and second ring to simultaneously slide relatively axially from over the second end of said stent, thereby releasing said ends of the stent from said catheter.

14. The stent delivery system of claim 13 wherein said expansible distal portion comprises a balloon mounted on a shaft of the catheter.

15. The stent delivery system of claim 14 wherein said stent is expanded by expansion of said balloon.

16. The stent delivery system of claim 13, said first and second sleeves, being formed from polyurethane.

17. The stent delivery system of claim 13, said sleeve being formed from any elastomer able to be expanded with a balloon angioplasty catheter, and formable into a thin-walled tube.

18. The stent delivery system of claim 13, said first end of said stent being a distal end, wherein said first sleeve fixes said stent at the distal end of said stent.

19. The stent delivery system of claim 13, said first and second sleeves, being formed in the shape of a cylinder.

20. The stent delivery system of claim 13, said rings being formed in the shape of a coil.

21. The stent delivery system of claim 13 wherein first and second rings are metal.

22. The stent delivery system of claim 13 wherein the ring is plastic.

23. The stent delivery system of claim 13 wherein said coil is plastic.

24. The stent delivery system of claim 13 wherein the coil is metal.

25. A stent delivery system comprising:
    a catheter comprising an expandable distal portion constructed and arranged for expanding the outer diameter of said catheter from a contracted state to an expanded state;
    a stent positioned around said distal portion of said catheter, said stent having a contracted condition and being expandable to an expanded condition, and being sized in said contracted condition to closely surround said catheter in the contracted state, said stent having at least an end portion defining a margin lying over said expandable portion of said catheter;
    a coil in the region of said distal portion of said catheter and positioned around said catheter, having a first end anchored to said catheter, and a second end defining a margin lying over said end portion of said stent; and a ring attached to said second end of said coil, the ring being within the coil and overlying said stent;

said coil and ring securing said end of said stent on said catheter when said catheter is in the contracted state, said catheter and stent cooperatively constructed and arranged to cause expansion of said catheter from said contracted state to said expanded state and to cause expansion of said stent, including said end of said stent, from said contracted condition to said expanded condition, thereby causing said coil and ring to simultaneously slide relatively axially from over the margin of said stent, thereby releasing said end of the stent from said catheter.

26. The stent delivery system of claim 25 wherein said coil is plastic.

27. The stent delivery system of claim 25 wherein said coil is metal.

28. The stent delivery system of claim 25 wherein said coil is rounded in cross-section.

29. The stent delivery system of claim 25 wherein said coil is flat ribbon-like in cross-section.

30. The stent delivery system of claim 26, wherein said expansible distal portion comprises a balloon mounted on a shaft of the catheter.

31. The stent delivery system of claim 30, wherein said stent is expanded by expansion of said balloon.

32. A stent delivery system comprising:

a catheter comprising an expansible distal portion constructed and arranged for expanding the outer diameter of said catheter from a contracted state to an expanded state;

a stent positioned around said distal portion of said catheter, said stent having a contracted condition and being expandable to an expanded condition, and being sized in said contracted condition to closely surround said catheter in the contracted state, said stent having a first and second end portion lying over said expandable portion of said catheter;

a first and second coil in the region of said distal portion of said catheter positioned around said catheter, each having a first end anchored to said catheter and a second end lying over a said end of said stent;

said first coil and said second coil separately engaging said stent at said first end and said second end respectively; and a first and second ring attached to said second ends of said coils, the rings overlying the stent;

said first and second coils and rings securing said ends of said stent on said catheter when said catheter is in the contracted state, said catheter and stent cooperatively constructed or arranged for expansion of said catheter from said contracted state to said expanded state to cause said first coil and ring to simultaneously slide relatively axially from over the margin of said stent first end and said second coil and ring to simultaneously slide relatively axially from over the margin of the stent second end, thereby releasing said ends of the stent from said catheter.

33. The stent delivery system of claim 32, wherein said expansible distal portion comprises a balloon mounted on a shaft of the catheter.

34. The stent delivery system of claim 33, wherein said stent is expanded by expansion of said balloon.

35. The stent delivery system of claim 32 wherein said first and second coils are plastic.

36. The stent delivery system of claim 32 wherein said first and second coils are metal.

37. The stent delivery system of claim 32 wherein said first and second coils are rounded in cross-section.

38. The stent delivery system of claim 33 wherein said first and second coils are flat ribbon-like in cross-section.

* * * * *

UNITED STATES PATENT AND TRADEMARK OFFICE
CERTIFICATE OF CORRECTION

PATENT NO. : 5,980,530

DATED : November 9, 1999

INVENTOR(S) : MARTIN R. WILLARD ET AL

It is certified that error appears in the above-identified patent and that said Letters Patent is hereby corrected as shown below:

On the face of the issued patent, please indicate:

[73] Assignee: Scimed Life Systems, Inc.
Maple Grove, Minn.

Signed and Sealed this

Twenty-ninth Day of August, 2000

Attest:

Q. TODD DICKINSON

*Attesting Officer*

*Director of Patents and Trademarks*